United States Patent
Quétin

[19]

[11] Patent Number: 5,769,853
[45] Date of Patent: Jun. 23, 1998

[54] BONE RASP

[76] Inventor: Roswitha Quétin, Jakob-Schober-Strasse 5, 69181 Leimen, Germany

[21] Appl. No.: 810,997
[22] Filed: Feb. 27, 1997

[30] Foreign Application Priority Data

Oct. 31, 1996 [DE] Germany .................. 196 44 015.7

[51] Int. Cl.$^6$ .................................................. A61B 17/56
[52] U.S. Cl. ................................ 606/85; 433/229; 606/79
[58] Field of Search ............................ 433/3, 201.1, 173, 433/215, 229; 606/79, 85

[56] References Cited

U.S. PATENT DOCUMENTS

| | | | |
|---|---|---|---|
| 5,342,362 | 8/1994 | Kenyon et al. | .................. 606/85 X |
| 5,417,693 | 5/1995 | Sowden et al. | .................. 606/85 |
| 5,601,561 | 2/1997 | Terry et al. | .................. 606/85 |

*Primary Examiner*—Nicholas D. Lucchesi
*Attorney, Agent, or Firm*—Diller, Ramik & Wight, PC

[57] ABSTRACT

The bone rasp (10) is provided with a rotatable drum-shaped rasp tool (36) with a cylinder wall (62) and a housing (12) provided with a cylindrical reception chamber (20) for the rasp tool (36) and a supply well (34) for bone pieces, extending radially from the reception chamber (20). The cylinder wall (62) of the rasp tool (36) is provided with a plurality of through bores (60) arranged adjacent to each other in several axially extending rows (58). The cylinder wall (62) comprises several teeth (68) respectively arranged between two adjacent through bores (60) and projecting beyond the portions (80) of the cylinder wall (62) located in front of them when viewed in radial extension of the rasp tool (36). The teeth (68), in plan view of the cylinder wall (62), are substantially tapered in V-shape, the tip pointing in rotational direction (70) of the rasp tool (36), and the tips of adjacent teeth (68) are connected, forming a cutting edge (72) with arcuate and pointed sections. The arcuate sections (74) are arranged directly behind the through bores (60) when viewed in rotational direction of the rasp tool (36). The cutting edges (72) of through bore rows (58) succeeding each other in rotational direction (70) of the rasp tool (36) radially project in different lengths beyond the cylinder wall (62).

7 Claims, 3 Drawing Sheets

BONE RASP

BACKGROUND OF THE INVENTION

The invention relates to a bone rasp as it is needed, for example, by implantologists, paradontologists, (oral) surgeons and dentists.

When implanting teeth, it is sometimes required to laterally set bone material to the jawbone so that the implanted tooth is surrounded by bone from all sides. The bone material to be supplemented is taken from the patient and manually crushed by means of a pair of forceps. This crushing method entails the problem that the portions splintering off the taken bone material have to be collected. In view of the fact that the amount of the bone material to be taken from the patient should be as small as possible, the manual crushing method by the forceps hence creates the danger that relatively large quantities of bone material have to be taken in order to still have left a sufficient amount of crushed material after the crushing procedure, since a relatively large portion has got lost (particles flying about which could not be collected).

Another method of crushing taken bone material known in prior art is to use a special rasp mechanism. The known system comprises a cutting plate non-rotatingly connected to a spindle and provided with radially extending linear cutting edges. The spindle is threaded with a cylindrical housing and can be manually turned from outside by means of an actuating tool. The actuating tool comprises a hexagonal socket which can be slipped upon a hexagonal insert bit of the spindle provided at the end facing away from the plate. By turning the spindle, the plate provided with cutting edges axially moves towards a screen bottom of the cylindrical housing. A collection cap is arranged below the screen bottom. By turning the spindle, the pressing force of the cutting plate against bone material arranged between the cutting plate and the screen bottom gradually increases. In the initial phase of contact between the cutting plate and the bone material, bone material may still be crushed. In the course of the further movement of the cutting plate, however, the pressure and pressing effects upon the bone material increase, which makes a further turning of the cutting plate almost impossible and particularly does no longer lead to a crushing by removing individual chips of bone material.

SUMMARY OF THE INVENTION

It is the object of the present invention to provide a bone rasp for crushing bone material which can be easily handled and by means of which only slightest loss amounts of rasped bone material occur, which are of no consequence.

This object is solved, according to the invention, with a bone rasp comprising a rotatable drum-shaped rasp tool with a cylinder wall, and a housing provided with a cylindrical reception chamber for the rasp tool and a supply well for bone pieces, extending radially from the reception chamber, wherein the cylinder wall of the rasp tool is provided with a plurality of through bores arranged adjacent to each other in several axially extending rows, the cylinder wall comprises several teeth respectively arranged between two adjacent through bores and projecting beyond the portions of the cylinder wall located in front of them when viewed in radial extension of the rasp tool, the teeth, in plan view of the cylinder wall, are substantially tapered in V-shape, the tip pointing in rotational direction of the rasp tool, and the tips of adjacent teeth are connected, forming a cutting edge with arcuate and pointed sections, the arcuate sections are arranged directly behind the through bores when viewed in rotational direction of the rasp tool, and the cutting edges of through bore rows succeeding each other in rotational direction of the rasp tool radially project in different lengths beyond the cylinder wall.

In a certain way, the bone rasp of the invention is comparable to a kitchen grater, wherein the grating or rasping tool moves relative to the material to be rasped. The bone rasp comprises a drum-shaped rasp tool with a cylinder wall rotatably accommodated within a reception chamber of a housing. The reception chamber communicates with a supply well extending radially to the cylindrical reception chamber. Into this supply well, bone material to be rasped is introduced, which then lies on the outer surface of the cylinder wall of the rasp tool. By means of a ram, the bone material can be radially pressed by force against the cylinder wall.

The rasp tool comprises a plurality of through bores extending through its cylinder wall. These through bores are respectively arranged adjacent each other in axially extending rows. Intermediate the through bores, there are teeth arranged on the outside of the cylinder wall which are, in plan view of the cylinder wall, of a tapered and V-shaped configuration, the tips of the teeth pointing in rotational direction of the rasp tool. Per row, the tips of the teeth, which point in rotational direction, are preferably arranged on the same level (on the same line extending parallel to the axial extension). Preferably, the tips of the teeth are located on a common line with the centers of the through bores arranged between the teeth. It is also possible, however, when viewed in rotational direction of the rasp tool, to displace the common line, on which the tips of the teeth are arranged, rearward relative to the centers of the through bores, so that they are particularly arranged at about the level of half the radius of the through bores.

The teeth tips adjacent each other and separated by through bores are interconnected by arcuate sections. Thereby, a plurality of cutting edges is created on the outside of the cylinder wall of the rasp tool, which comprise tapering sections of the teeth and arcuate sections connecting the latter. These arcuate sections are particularly circle sections.

The thus configured cutting edges on the outside of the cylinder wall have different heights. This means that cutting edges succeeding each other in rotational direction of the rasp tool project in different lengths beyond the portions of the cylinder wall lying directly before them. Suitably, the height offset between two cutting edges succeeding each other in rotational direction of the rasp tool varies alternately.

In the bone rasp according to the invention, the through bores are located in close proximity to the cutting edges, the arcuate sections of the cutting edges extending tangentially to the edges of the through bores, i.e., the edges partially define the through bores. The steep flanks of the cutting edges pointing in rotational direction of the rasp tool at least extend radially, preferably at an acute angle with respect to the radial extension, so that the cutting edges form an undercut.

With a bone rasp of the afore-mentioned kind according to the invention, astonishable results could be achieved in tests. It was possible, for example, to chip or rasp the hardest human bone material from the front region of the lower jaw (corticalis compacta) while employing only small forces. The amount of bone material left at the rasp tool was insignificant compared with the rasp material; in this respect, the bone rasp according to the invention has a high utilization ratio of almost 1 (ratio of bone material to be rasped to bone material rasped).

In an advantageous embodiment of the invention, the through bores are formed in the cylinder wall of the rasp tool so as to be slightly offset to the radial extension. With an outer diameter of the rasp tool of 3 to 5 cm, the offset preferably amounts to 1.5 mm.

With a rasp tool having an outer diameter of about 3 to 5 cm, the height offset of adjacent cutting edges preferably amounts to 1/10 mm. The lower cutting edges particularly amount to 0.25 mm, so that the higher cutting edges consequentially project by 0.35 mm. It has turned out that it is sufficient to provide only two cutting edges with different heights on the outside of the cylinder wall of the rasp tool, these cutting edges alternately succeeding each other in rotational direction of the rasp tool.

To be able to reliably and conveniently collect the rasp material, an embodiment of the invention provides for a collection cap at the housing, which collection cap is releasably connectable to the housing and closes the reception chamber accommodating the rasp tool at its one axial end in the attached state.

Preferably, the rasp tool comprises an axially projecting drive shaft connectable to a hand toggle. In experiments, such a hand toggle has proved to be an easily operable actuator for manually rotating the rasp tool. In comparison with a hand crank in particular, a hand toggle with two diametrically opposing and radially projecting arms has advantages if the dimensional tolerances of the bone rasp are extremely small. For such a hand toggle rather prevents a "jamming" of the supporting shaft of the rasp tool, so that no complicated roller bearings or roll body bearings have to be used to support the shaft on the housing.

Preferably, the housing of the inventive bone rasp is provided with a clamp-like support with an adjustable clamp to be able to attach the bone rasp at a tabletop or the like edge. In the clamped state of the bone rasp, the rasp tool is preferably inclined towards the collection cap.

As an alternative to a manually operable rotating element for rotating the rasp tool, it is also possible to use a motor.

Within the scope of this description, the inventive bone rasp is described with respect to a drum-shaped rasp tool. But it is as well possible to realize the inventive configuration and arrangement of the teeth of the rasp tool on a plate or circular surface. Via a well arranged eccentrically to the axis of the plate, bone material is supplied which is ground upon rotation of the plate and falls into a reception chamber arranged below the plate. The through bores axially penetrate the plate and are particularly arranged along radial lines. The configuration of the cutting edges is similar to that according to the above description.

BRIEF DESCRIPTION OF THE DRAWINGS

Hereinafter, an embodiment of the invention is explained in detail with respect to the Figures, in which:

FIG. 1 shows a rasp 10 for bone material in side view. The rasp 10 comprises a housing 12 made of metal, particularly of stainless steel, and comprising a clamping foot 14. By means of the clamping foot 14, the housing 12 can be clamped to the free edge of, e.g., a tabletop or working plate 16, as is shown in FIG. 1.

Figure 1:
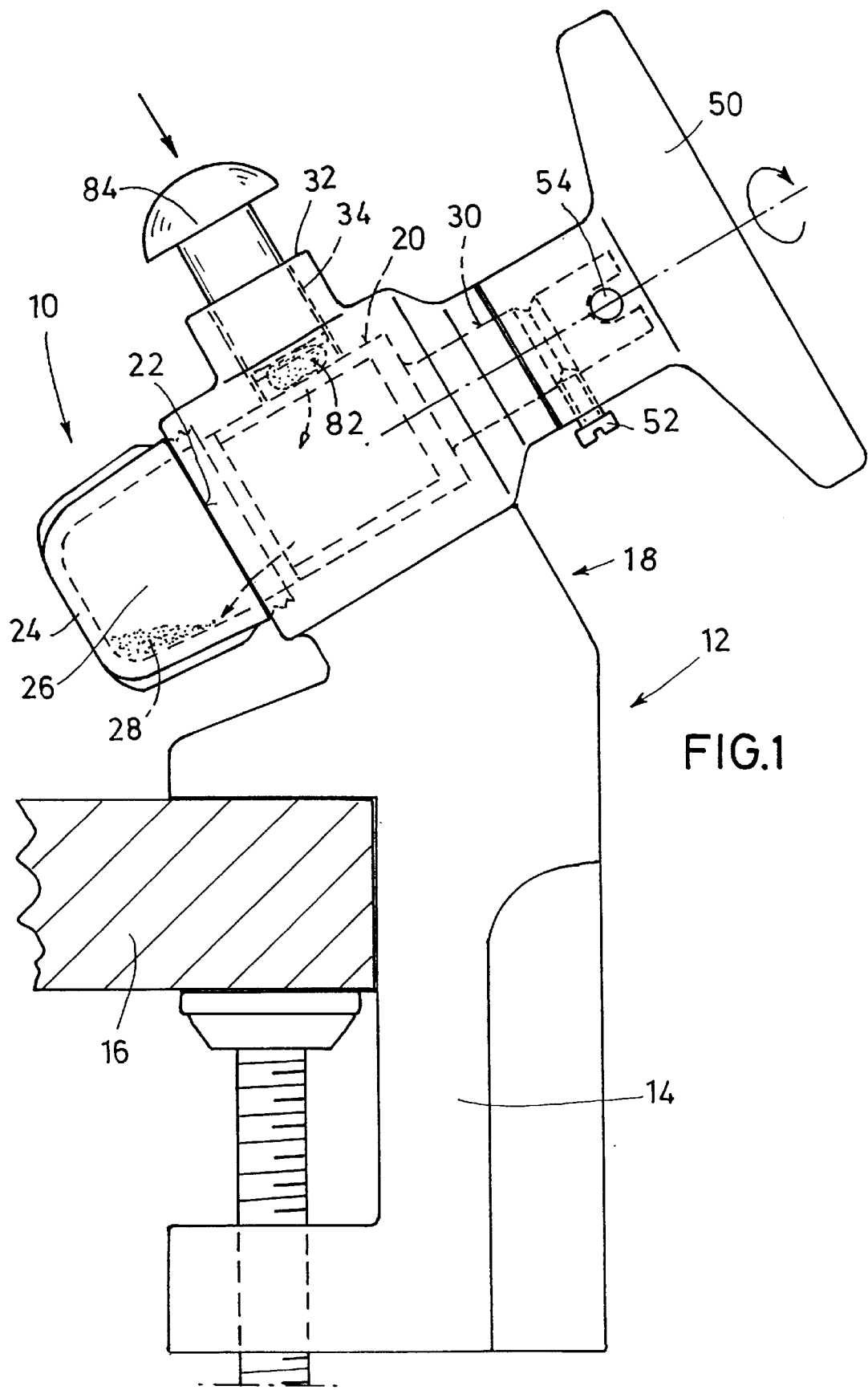
FIG. 1 is a side view of a bone rasp with a clamping foot set upon the projecting edge of a plate.

Above the clamping foot 14, the housing 12 is angled. In this angled region 18, the housing 12 is provided with a cylindrical reception chamber 20 open towards an axial end 22. In this region, a screw cap 24 comprising an inner depression 26 for receiving rasp material 28 can be screwed onto the housing 12.

On its side facing away from the screw cap 24, the reception chamber 20 is connected to a coaxial through opening 10 terminating on that side of the angled region 18 of the housing 12 opposite the screw cap 24. A filling or supply well 34 extending to the upper end 32 of the housing 12 extends radially to the cylindrical reception chamber 20 on the upper end 32 of the housing 12 facing away from the clamping foot 14.

Figure 2:
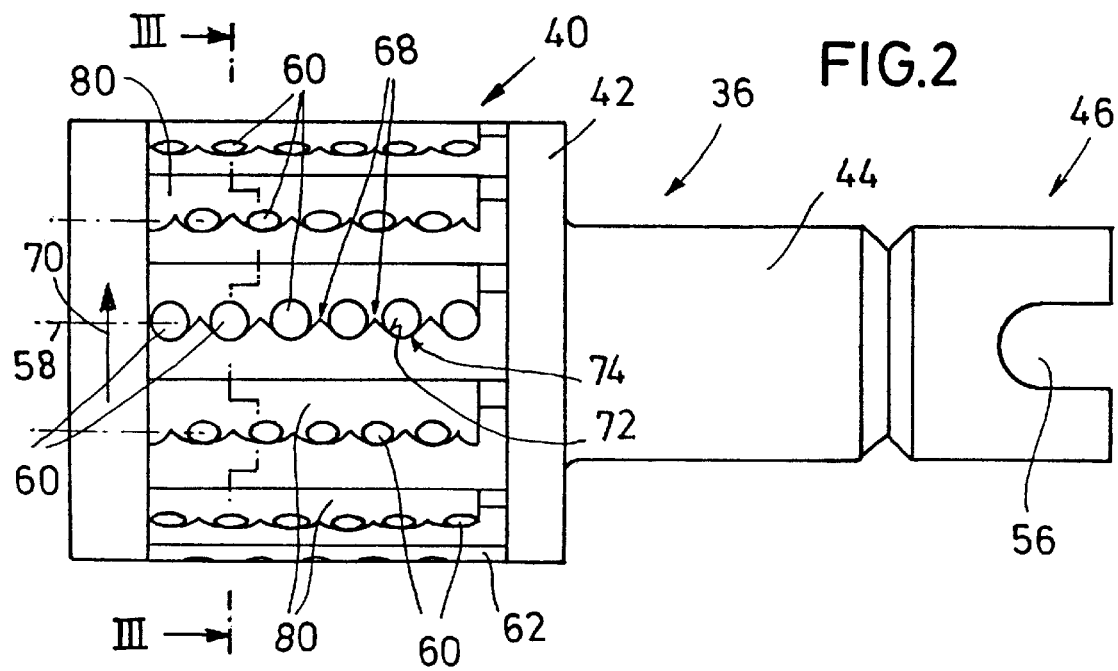
FIG. 2 is a plan view of the rasp tool in radial direction.
Figure 3:
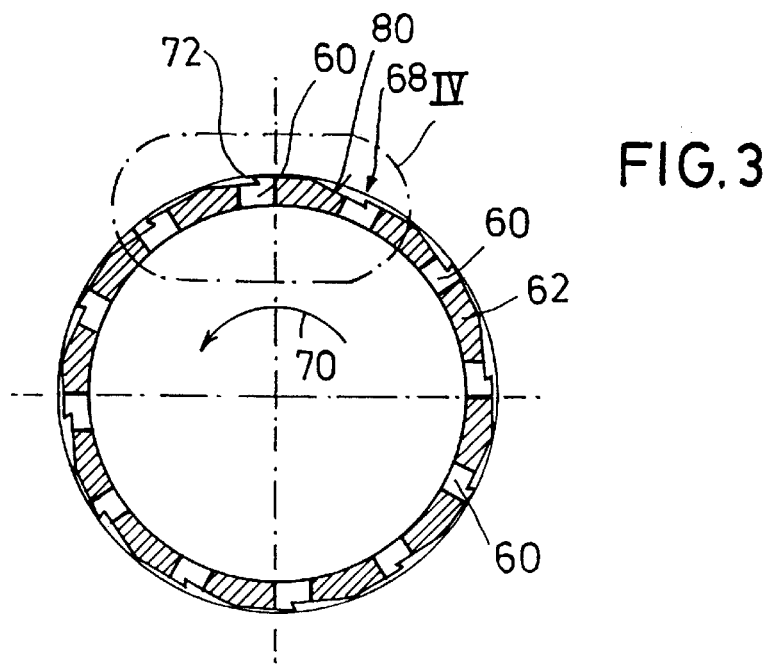
FIG. 3 is a section along line III—III of FIG. 2.

Via the open axial end 22 of the reception chamber 20, a rasp tool 36 can be inserted therein; an illustration of this rasp tool is shown in FIG. 2. The rasp tool 36 comprises a unilaterally open drum portion 40 with a coaxial shaft 44 following the closed end 42. When the rasp tool 36 is installed, this shaft 44 extends through the through opening 30 of the housing 12 and projects beyond the latter. Then, a hand toggle 50 is pushed over the projecting end 46, which can be fixed against axial displacements on the shaft 44 via a radial attachment screw 52. The fixed coupling of hand toggle 50 and shaft 44 is effected by a radial bolt 54 of the hand toggle 50, which is immersed into a radial continuous thread 56 of the shaft 44.

Figure 4:
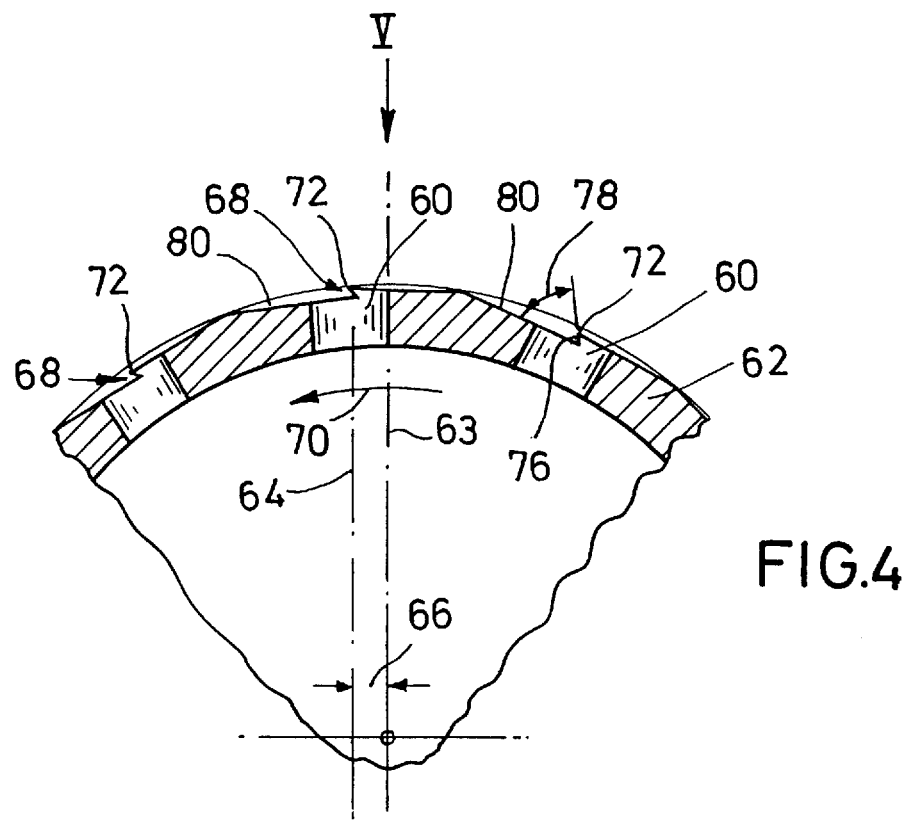
FIG. 4 is an enlarged representation of the region indicated at IV in FIG. 3.

According to FIGS. 2 to 5, the drum portion 40 of the rasp tool 36 comprises several through bores 60 arranged along axially extending rows 58 and formed in the cylindrical wall 62 of the drum portion 40. As is best seen in FIG. 4, the bores 60 are offset to the radial extension in circumferential direction (see line 63 of FIG. 4), so that an offset develops between the central axes 64 of the through bores 60 and the radial extension 63. This offset amounts to 1.5 mm, the diameter of the bores amounting to 3 mm.

On the outside of the cylinder wall 62, there is a plurality of tapering, substantially V-shaped projections 68 pointing in rotational direction 70 of the rasp tool 36. These pointed teeth 68 form part of wavelike cutting edges 72 comprising circular arc sections 74 between the pointed teeth 68. In the region of these circular arc sections 74, the cutting edges 72 form the edge of the bores 60 over a certain circumferential portion. Particularly from FIG. 4, it is to be seen that the height of the cutting edges 72 varies alternately from one cutting edge to the other, namely by 0.15 mm. The height of the cutting edges 72 of one row amounts to, e.g., 0.35 mm, while the cutting edges 72 of the neighboring rows are 0.2 mm high. From the illustration according to FIG. 4, it further results that the cutting edges 72 comprise undercuts, i.e. , that their steep flanks 76 form an acute angle 78 with the portions 80 of the cylinder wall 62 arranged directly before the cutting edges 72 and the bores 60 when viewed in rotational direction 70. The portions 80 are created by flattening the cylindrical outside of the cylinder wall 62.

Figure 5:
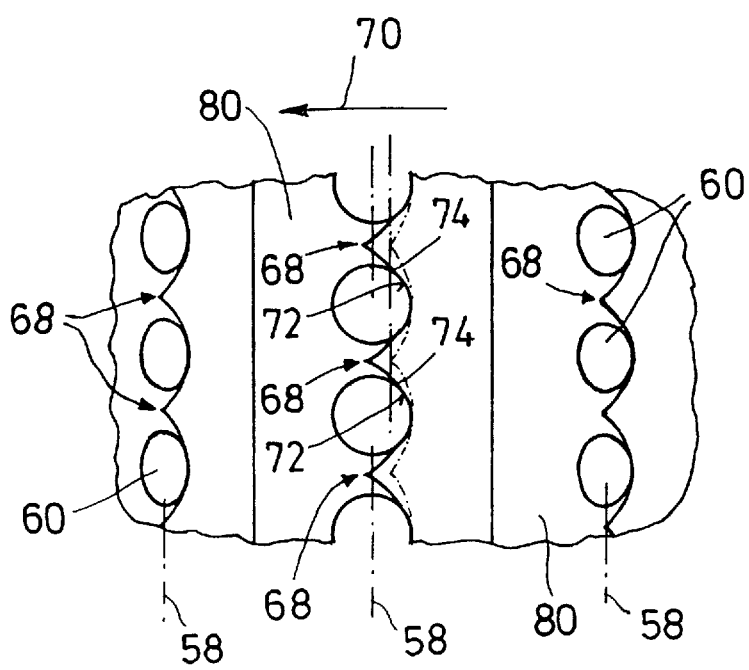
FIG. 5 is a plan view of the rasp tool according to V of FIG. 4.

As indicated in FIG. 5, the position of the pointed teeth 68 can vary relative to the orientation of the rows 58 of the bores 60. FIG. 5 shows, in continuous lines, the case that the pointed ends of the teeth 68 and the centers of the bores 60 are arranged on a common line. It is also imaginable, however, that the teeth 68 lag behind the centers of the bores 60 when viewed in rotational direction 70. Particularly, the teeth 68 lie by 0.4 mm behind the front ends of the edges of the through bores 60 when viewed in rotational direction, or, in other words, the teeth 68 are ahead of the centers of the through bores 60 by 1.1 mm when the diameter of the through bores 60 amounts to 3 mm.

For rasping bone material, bone pieces 82 are introduced into the supply well 34 and pressed against the rotating outside of the cylinder wall 62 of the drum portion 40 of the rasp tool 36, which is provided with the projecting teeth 68 and the cutting edges 72. Through the through bores 60 located directly in front of the cutting edges 72, the rasp material is transported into the interior of the drum portion 40 of the rasp tool 36. Due to the inclination of the rasp tool 36 towards the open axial end 22 of the reception chamber 20 of the housing 12, the rasp material 28 arrives in the screw and collection cap 24.

What is claimed is:

1. A bone rasp comprising a rotatable drum-shaped rasp tool (36) with a cylinder wall (62), a housing (12) provided with a cylindrical reception chamber (20) for the rasp tool (36) and a supply well (34) for bone pieces extending radially from the reception chamber (20), the cylinder wall (62) of the rasp tool (36) is provided with a plurality of through bores (60) arranged adjacent to each other in a plurality axially extending rows (58), the cylinder wall (62) includes at least one tooth (68) between two adjacent through bores (60) and projecting beyond portions (80) of the cylinder wall (62) located in front of said at least one tooth, said at least one tooth (68), being of a substantially tapered V-shape configuration a tip of said at least one tooth (68) pointing in rotational direction (70) of the rasp tool (36), tips of adjacent teeth (68) are connected, forming a cutting edge (72) with arcuate sections (74) arranged directly behind the through bores (60) when viewed in rotational direction (70) of the rasp tool (36), and the cutting edges (72) of through bore rows (58) succeeding each other in rotational direction (70) of the rasp tool (36) radially project in different lengths beyond the cylinder wall (62).

2. The bone rasp according to claim 1, wherein the projecting length of the cutting edges (72) is from row to row different.

3. The bone rasp according to claim 1, wherein the through bores (60) are formed in the cylinder wall (62) of the rasp tool (36) so as to be offset.

4. The bone rasp according to claim 1, wherein the front edges of the teeth (68) pointing in rotational direction (70) of the rasp tool (36) form an undercut.

5. The bone rasp according to claim 1, wherein the teeth (68) and the through bores (60) are axially offset with respect to each other from one row (58) to the other (58).

6. The bone rasp according to claim 1, wherein a collection cap (24) for collecting bone material (28) is releasably connectable with the housing (12).

7. The bone rasp according to claim 2, wherein the through bores (60) are formed in the cylinder wall (62) of the rasp tool (36) so as to be offset.

* * * * *